United States Patent [19]

Maruyama

[11] Patent Number: 5,048,535
[45] Date of Patent: Sep. 17, 1991

[54] METHOD AND APPARATUS FOR DETECTING QRS COMPLEX OF ECG

[75] Inventor: Mitsuya Maruyama, Tokyo, Japan

[73] Assignee: Fukuda Denshi Co., Ltd., Tokyo, Japan

[21] Appl. No.: 536,829

[22] Filed: Jun. 12, 1990

[30] Foreign Application Priority Data

Jun. 23, 1989 [JP] Japan ................................. 1-161920

[51] Int. Cl.$^5$ ........................................ A61B 5/0456
[52] U.S. Cl. ................................................ 128/708
[58] Field of Search ........................................ 128/708

[56] References Cited

U.S. PATENT DOCUMENTS 4,617,938 10/1986 Shimoni et al. ..................... 128/708

Primary Examiner—William E. Kamm
Attorney, Agent, or Firm—Sughrue, Mion, Zinn, Macpeak & Seas

[57] ABSTRACT

A method for detecting a QRS complex of an ECG is provided. The method includes the steps of inputting an ECG signal, setting a first threshold value based on a peak value of a QRS complex of the ECG signal, setting a second threshold value by estimating a noise level proprotional to the amount of noise included in the ECG signal comparing the first threshold value with the second threshold value, deeming a larger one of the first and second threshold values to be a third threshold value for detecting the QRS complex, detecting the QRS complex by using the threshold value for detecting the QRS complex, and outputting a synchronous signal synchronized with the detected QRS complex.

5 Claims, 3 Drawing Sheets

METHOD AND APPARATUS FOR DETECTING QRS COMPLEX OF ECG

BACKGROUND OF THE INVENTION

1. Field of the Invention

The present invention relates to a method and an apparatus for detecting a QRS complex of an electrocardiogram (ECG).

More particularly, it relates to a method and an apparatus for detecting a QRS complex of an ECG, in which the QRS complex is detected and a synchronous signal synchronized with the detected QRS complex is output.

2. Description of the Related Art

Generally, a QRS complex is a wave in which Q, R and S waves of an ECG are combined, the QRS complex appearing just before a ventricle of the heart contracts. Its occurrence means that the ventricle is in the process of heart excitation.

Hence, when a synchronous signal synchronized with the QRS complex is output, it is used to count the heart beat number.

Before the synchronous signal is output, the QRS complex should first be detected. With the conventional method of detecting a QRS complex of an ECG, a threshold value is computed by using a peak value of a first QRS complex of an ECG, and a wave with a value beyond the threshold value is detected as a second QRS complex. Afterwards, a synchronous signal which is synchronized with the second QRS complex is output. With the conventional method, the threshold value computed based on the peak value of the QRS complex is fixed. Accordingly, the influence of noise included the ECG is not considered with the conventional device. Accordingly, the noise can be accidentally detected as the QRS complex.

SUMMARY OF THE INVENTION

An object of the present invention is to improve the accuracy for detecting a QRS complex.

The above-mentioned object can be achieved by a method for detecting a QRS complex of an ECG. In the method of the present invention, the steps of inputting an ECG signal, setting a first threshold value based on a peak value of a QRS complex of the ECG signal, setting a second threshold value by estimating a noise level proportional to the amount of noise included in the ECG signal, comparing the first threshold value with the second threshold value, deeming the larger one of the first and second threshold values to be a third threshold value for detecting a QRS complex, detecting the QRS complex by using the third threshold value for detecting the QRS complex, and outputting a synchronous signal synchronized with the detected QRS complex are performed.

The present invention also included an apparatus for detecting a QRS complex of an ECG, the apparatus having a first threshold computing portion which inputs an ECG signal and outputs a first threshold value based on a peak value of a QRS complex of the ECG signal, a second threshold computing portion which inputs the ECG signal and outputs a second threshold value by estimating a noise level proportional to the amount of noise included in the ECG signal, a threshold comparing portion which inputs the first and second threshold values, compares the values of them, and outputs a larger one of them as a third threshold value for detecting a QRS complex, and a synchronous signal outputting portion which inputs the third threshold value for detecting the QRS complex and the ECG signal, detects the QRS complex of the ECG signal by using the third threshold value for detecting QRS, and outputs a synchronous signal synchronized with the detected QRS complex.

BRIEF DESCRIPTION OF THE DRAWINGS

Further features and advantages of the present invention will be apparent from the ensuring description with reference to the accompanying drawings, wherein.

DESCRIPTION OF THE PREFERRED EMBODIMENTS

Figure 1:
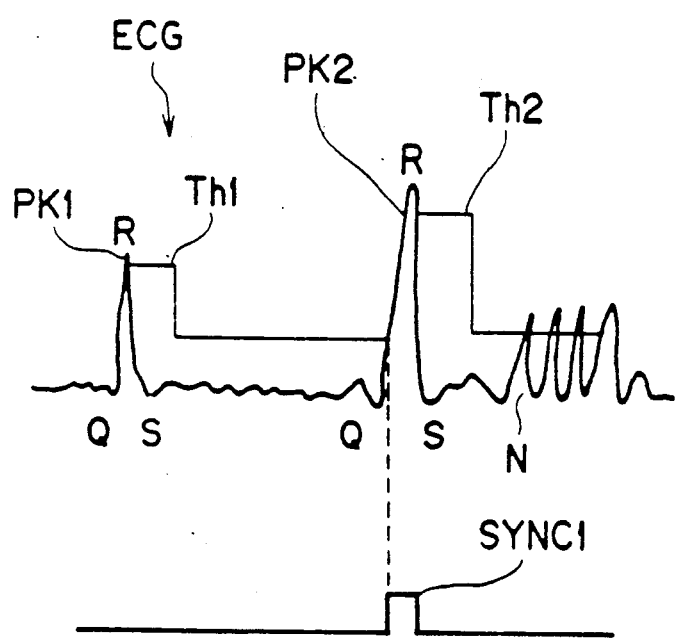
FIG. 1 is an explanatory drawing of the prior art.

FIG. 1 is an explanatory drawing of a prior art system, wherein a conventional method for detecting a QRS complex of an ECG is shown.

Referring to FIG. 1, a threshold value Th1 is computed by using a peak value PK1 of a first QRS complex of an ECG, and a wave with a value beyond the threshold value Th1 is detected as a second QRS complex. Next, a synchronous signal SYNC1 synchronized with the second QRS complex is output.

However, the threshold value computed based on the peak value of the QRS complex is fixed.

As a result, in the prior art as shown in FIG. 1, the influence of noise included in the ECG is not considered at all.

Hence, when the noise becomes large, it is detected accidentally by the fixed threshold values as the QRS complex.

For example, in FIG. 1, a threshold value Th2 computed with a peak value PK2 of a second QRS complex is used in order to detect a next third QRS complex (not shown).

However, when noise N is included in the ECG, the noise N is detected accidentally by using the threshold value Th2 as the third QRS complex.

Accordingly, the problem with the prior art is that the accuracy for detecting a QRS complex is low.

Figure 2:
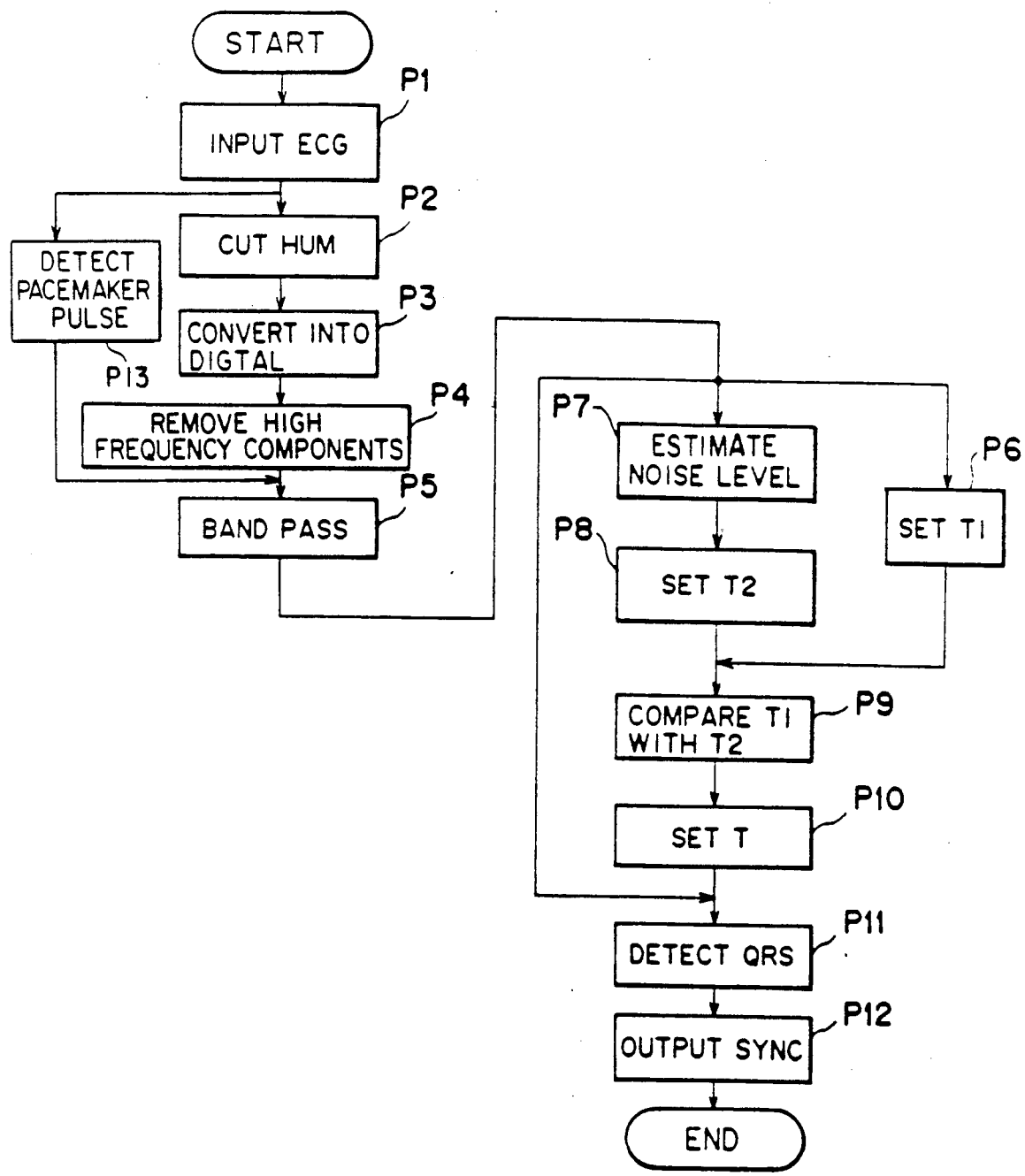
FIG. 2 is a flow chart of a method in accordance with the present invention.

FIG. 2 is a drawing of an embodiment of a method in accordance with the present invention.

First, an electrocardiogram (ECG) is input from the living body of a patient, in step P1.

In step P2, any hum included in the ECG is removed.

Then, the ECG, from which the hum is removed, is converted into a digital signal from an analog signal in step P3.

The high frequency component of the ECG is removed in step P4, and the signal level of the ECG is passed in a certain bandwidth in step P5. A step P13, in which a pacemaker pulse is identified and a signal corresponding to the pacemaker pulse is output, is performed in parallel with step P2 through P4 to remove the pacemaker pulse from the ECG signal at step P5.

Thereafter, the ECG is treated in steps P6 and P7.

In step P6, a peak value of the ECG is detected, and a first threshold value T1 is determined based on the peak value of the ECG.

In step P7, a level of noise included in ECG is estimated, and a second threshold value T2 is determined based on the estimated noise level in step P8.

The sizes of the first and second threshold values T1 and T2 are compared in step P9, and a larger one of the above threshold values T1 and T2 is set as a third threshold value T for detecting the QRS complex in the ECG in step P10.

In step P11, the QRS complex is detected on the basis of the QRS complex detecting threshold value T and the ECG treated in step P5.

In step P12, a synchronous signal synchronized with the detected QRS complex is output.

Figure 3A:
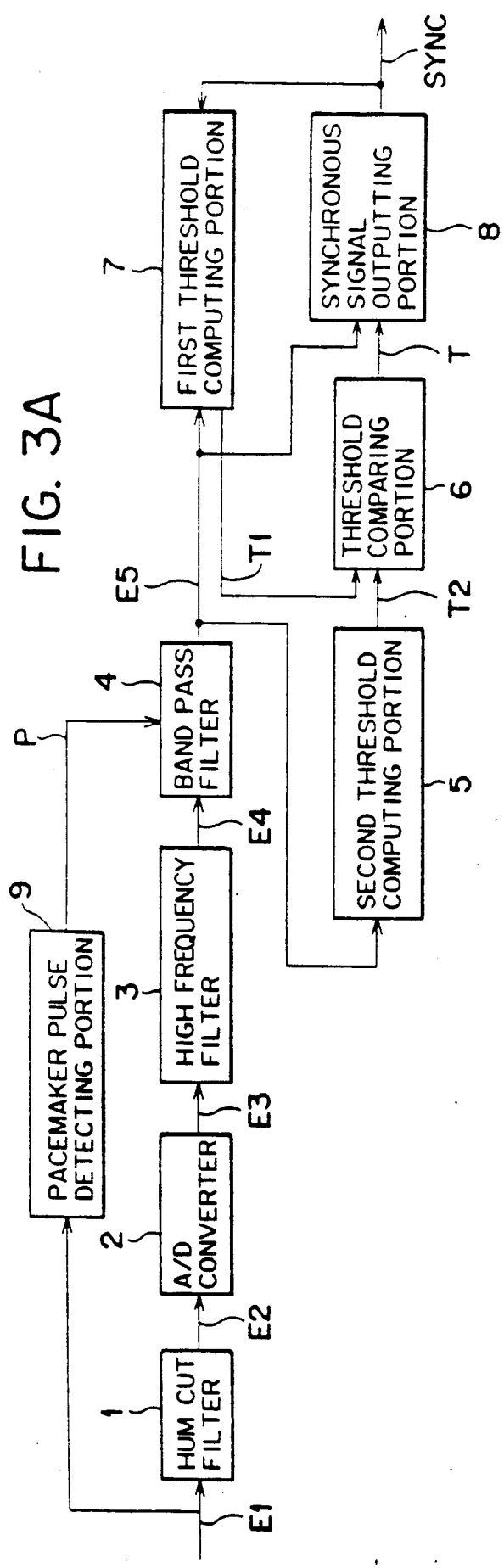
FIG. 3A is a drawing of an embodiment of an apparatus in accordance with the present invention.

FIG. 3A is a drawing of an embodiment of an apparatus in accordance with the present invention, wherein reference numeral 1 shows a hum cut filter, 2 is an A/D converter, 3 is a high frequency filter, 4 is a band pass filter, 5 is a second threshold computing portion, 6 is a threshold comparing portion, 7 is a first threshold computing portion, 8 is a synchronous signal outputting portion, and 9 is a pacemaker pulse detecting portion.

Figure 3C:
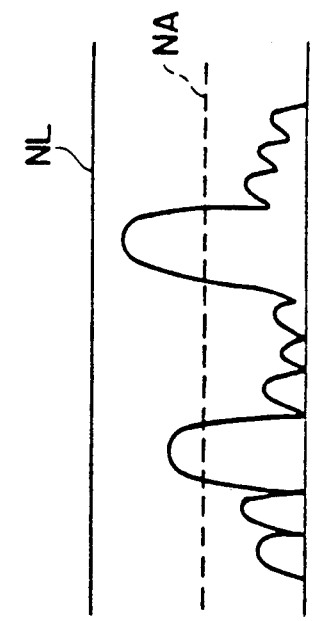
FIG. 3C is another explanatory drawing for operating the apparatus of FIG. 3A.
Figure 3B:
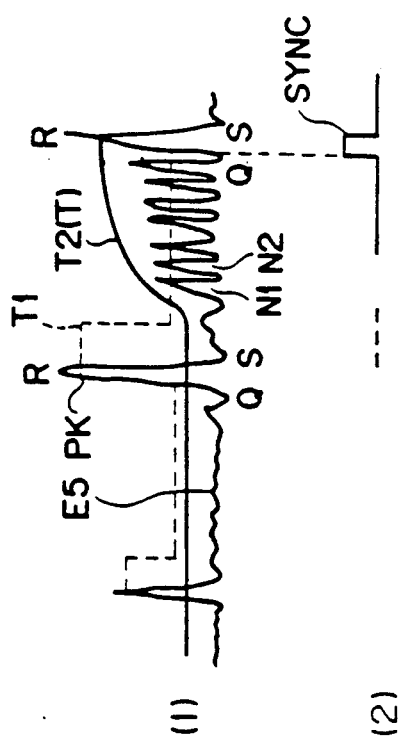
FIG. 3B is an explanatory drawing for operating the apparatus of FIG. 3A.

FIG. 3B is an explanatory drawing for the operation of the apparatus of FIG. 3A, wherein representative waveforms of the various signals and thresholds are shown.

FIG. 3C is another explanatory drawing for the operation of the apparatus of FIG. 3A, wherein the technique for estimating a noise level is shown.

ECG signal E1 led from the living body of a patient is input into the hum cut filter 1 and the pacemaker pulse detecting portion 9.

Hum included in the ECG signal E1 is removed in the hum cut filter 1, and ECG signal E2 without hum is output.

The ECG signal E2 is input into the A/D converter 2, where it is converted from an analog signal into a digital signal. Consequently, digital ECG signal E3 is output from the A/D converter 2.

The digital ECG signal E3 is input into the high frequency filter 3, wherein high frequency component of it is removed.

Accordingly, ECG signal E4, with no high frequency component, is output from the high frequency filter 3, and it is input into the band pass filter 4.

In the band pass filter 4, the signal level of the ECG signal in the bandwidth of interest is passed, whereby ECG signal E5 represented by FIG. 3B, graph (1) is output from the ECG signal. It will be appreciated that the waveform of FIG. 3B is a representation of the peak signal levels of the digitized ECG signal E5.

Since pulse P output from the pacemaker pulse detecting portion 9 is also input into the band pass filter 4, the pulse P is removed.

As a result, the pulse P corresponding to a pacemaker pulse is not included in the ECG signal E5.

The ECG signal E5 is input into the first and second threshold computing portions 5 and 7, and to the synchronous signal outputting portion.

In the second threshold computing portion 5, a level of noise included in the ECG signal E5 is estimated as shown in FIG. 3C.

That is to say, an average peak value NA of the ECG signal E5 is computed by means of deeming the ECG signal E5 to be a half wave rectified sine wave.

If the average peak value NA is considered the noise level, when the amount of noise which is included in the ECG signal E5 increases, the larger amount of noise is detected accidentally as the QRS complex.

Hence, in order that there is sufficient margin to detect the QRS complex, a level NL, which is twice the average peak value NA, is estimated to be the noise level.

A formula for expressing the level NL is as follows.

$$NL = 2NA = 4Y_n = 4\{Y_{n-1} + (1/K)(X_n - Y_{n-1})\}$$

In the above formula, $X_n$ represents the value of an input signal at time n into the second threshold computing portion 5, and $Y_n$ and $Y_{n-1}$ represents the value of an output signal at times n and n−1 from the same portion 5, respectively.

Based on noise N1, N2 . . . included in the ECG signal E5 (see FIG. 3B, graph (1)), the noise level NL is estimated as described above and as shown in FIG. 3C, and it is set as the second threshold value T2 (see FIG. 3B, graph (1)).

As is apparent from FIG. 3B, the second threshold value T2 is proportional to the amount of noise N1, N2 . . . and is larger than them.

The second threshold value T2 is input into the threshold comparing portion 6.

On the other hand, in the first threshold computer portion 7, a first threshold value T1 is computed based on a peak value PK (see FIG. 3B, graph (1)) of the QRS complex of the ECG signal E5, which first threshold value T1, is input into the threshold comparing portion 6.

Accordingly, in the threshold comparing portion 6, the magnitudes of the first threshold value T1 and the second threshold value T2 are compared.

Since the second threshold value T2 is larger than the first threshold value T1 for each noise N1, N2 . . . , it is considered a third threshold value T for detecting the QRS complex, which threshold value T is input into the synchronous signal outputting portion 8.

In the synchronous outputting portion 8, wherein the ECG signal E5 has been already input, a next QRS complex is detected by using the third threshold value T for detecting the QRS complex. Thereafter, a synchronous signal SYNC synchronized with the detected QRS complex is output, as shown in FIG. 3B, graph (2).

According to the present invention, the second threshold value T2 is set by estimating a noise level proportional to the amount of noise included in the ECG signal E5, which second threshold value T2 is compared with the first threshold value T1 computed based on the peak value PK of the ECG signal E5.

Thereby, a larger one of the first and second threshold values T1 and T2 is deemed to be the third threshold value T for detecting the QRS complex, with which value T a next QRS complex can be detected.

Consequently, since the influence of noise is considered sufficiently by the present invention, a large noise is not detected accidentally as a QRS complex like the prior art does.

Hence, the accuracy for detecting QRS complex has been improved remarkably.

I claim:

1. A method for detecting a QRS complex of an ECG, comprising:
  inputting an ECG signal;

setting a first threshold value based on a peak value of a first QRS complex of said ECG signal;

setting a second threshold value by estimating a noise level proportional to an amount of noise included in said ECG signal;

comparing said first threshold value with said second threshold value;

setting the larger one of said first and second threshold values as a third threshold value for detecting a second QRS complex;

detecting said second QRS complex by using said third threshold value; and outputting a synchronous signal synchronized with said detected second QRS complex.

2. A method for detecting a QRS complex of an ECG according to claim 1, wherein said second threshold value setting step further comprises the steps of:

estimating an average peak value of said amount of noise of said ECG signal; and setting said second threshold value equal to twice said average peak value.

3. An apparatus for detecting a QRS complex of an ECG, comprising:

first threshold computing means receiving an ECG signal for generating a first threshold value based on a peak value of a first QRS complex of said ECG signal;

second threshold computing receiving said ECG signal for generating a second threshold value by estimating a noise level proportional to an amount of noise included in said ECG signal;

threshold comparing means receiving said first and second threshold values for comparing said first and second threshold values and outputting a larger one of them as a third threshold value for detecting a second QRS complex; and synchronous signal outputting means receiving said third threshold value for detecting said second QRS complex and said ECG signal for detecting said second QRS complex of said ECG signal based on said third threshold value, and for outputting a synchronous signal synchronized with said detected second QRS complex.

4. The apparatus of claim 3, further comprising means for removing a pacemaker pulse from said ECG signal.

5. The apparatus of claim 3, wherein said ECG signal is a digital filtered ECG signal and wherein said apparatus further comprises:

converting means receiving an analog ECG signal for producing a digital ECG signal; and filter means receiving said digital ECG signal for filtering said ECG signal so as to produce said digital filtered ECG signal.

* * * * *